United States Patent [19]

Kaplan et al.

[11] 4,382,938

[45] May 10, 1983

[54] IMIDAZO[1,2-A] PYRIDINE DERIVATIVES AND THEIR APPLICATION AS PHARMACEUTICALS

[75] Inventors: Jean-Pierre Kaplan, Bourg la Reine; Pascal George, Vitry sur Seine, both of France

[73] Assignee: Synthelabo, Paris, France

[21] Appl. No.: 313,601

[22] Filed: Oct. 21, 1981

[30] Foreign Application Priority Data

Oct. 22, 1980 [FR] France .................. 80 22537

[51] Int. Cl.³ .................. A61K 31/435; C07D 471/04
[52] U.S. Cl. .................. 424/256; 544/58.4; 544/127; 544/362; 546/121
[58] Field of Search .................. 544/58.4, 127, 362; 546/121; 424/246, 248.54, 250, 248.52, 256

[56] References Cited

U.S. PATENT DOCUMENTS 3,336,194  8/1967  Shen .................. 260/326.13 A

FOREIGN PATENT DOCUMENTS 1076089  7/1967  United Kingdom .

OTHER PUBLICATIONS

Almirante et al., I, J. Med. Chem., vol. 8, (1965) pp. 305–312.
Almirante et al., II, J. Med. Chem., vol. 12, (1969) pp. 123–126.

Primary Examiner—Henry R. Jiles
Assistant Examiner—Bernard Dentz
Attorney, Agent, or Firm—Wegner & Bretschneider

[57] ABSTRACT

Imidazo[1,2-a] pyridines of the formula:

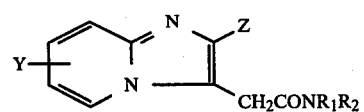

and their acid addition salts in which Y represents a hydrogen or halogen atom or a $C_{1-4}$ alkyl radical, Z represents a naphthyl radical or a radical

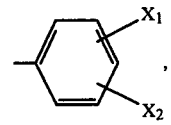

in which each of $X_1$ and $X_2$ independently of one another is a hydrogen or halogen atom, a $C_{1-4}$ alkoxy radical, a $C_{1-6}$ alkyl radical or $CF_3$, $CH_3S-$, $CH_3SO_2-$, $-NO_2$, $-NH_2$ or $-NHCOCH_3$, and each of $R_1$ and $R_2$ independently of one another represents a hydrogen atom, a straight or branched $C_{1-5}$ alkyl radical which is unsubstituted or substituted by one or more halogen atoms or hydroxyl, $-N(C_{1-4}$ alkyl$)_2$, carbamoyl or $C_{1-4}$ alkoxy radicals, allyl, propargyl, a $C_{3-6}$ cycloalkyl radical, benzyl, or phenyl, not both $R_1$ and $R_2$ being hydrogen, or $-NR_1R_2$ represents a heterocyclic ring containing from 3 to 6 carbon atoms, or a heterocyclic ring of the formula

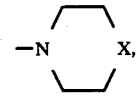

in which X is O, S, CHOR' or $>$N—R, R' being hydrogen or benzyl and R being hydrogen, a $C_{1-4}$ alkyl radical, or phenyl which is unsubstituted or substituted by methoxy or a halogen atom, which may be made from the corresponding acids, have valuable pharmacological properties, especially anxiolytic, anti-anoxic, sleep-inducing, hypnotic and anticonvulsant properties.

12 Claims, No Drawings

IMIDAZO[1,2-a] PYRIDINE DERIVATIVES AND THEIR APPLICATION AS PHARMACEUTICALS

DESCRIPTION

The present invention relates to imidazo [1,2-a] pyridine derivatives, useful in therapy and their preparation.

Imidazo [1,2-a] pyridines have already been described in the literature, for example in British Pat. Nos. 991,589 and 1,076,089 and in various other publications.

The compounds of the present invention have the formula (I)

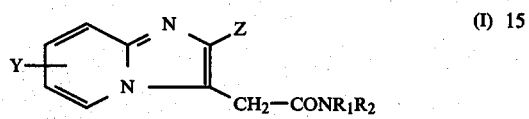
(I)

in which Y represents a hydrogen or halogen atom or a $C_{1-4}$ alkyl radical, Z represents a naphthyl radical or a radical

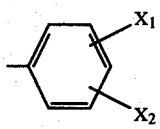

in which each of $X_1$ and $X_2$ independently of one another is a hydrogen or halogen atom, a $C_{1-4}$ alkoxy radical, a $C_{1-6}$ alkyl radical or $CF_3$, $CH_3S$, $CH_3SO_2$ or $NO_2$ and each of $R_1$ and $R_2$ independently of one another represents a hydrogen atom, a straight or branched $C_{1-5}$ alkyl radical which is unsubstituted or substituted by one or more halogen atoms, hydroxyl, $N(C_{1-4}alkyl)_2$, carbamoyl or $C_{1-4}$ alkoxy radicals, an allyl radical, a propargyl radical, a $C_{3-6}$ cycloalkyl radical, a benzyl radical or a phenyl radical, not both $R_1$ and $R_2$ being hydrogen, or $NR_1R_2$ represents a heterocyclic ring containing from 3 to 6 carbon atoms, or a heterocyclic ring of the formula,

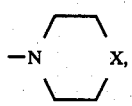

in which X is O, S, CHOR' or >NR, R' being hydrogen or benzyl and R being hydrogen, a $C_{1-4}$ alkyl radical or phenyl which is unsubstituted or substituted by methoxy or a halogen atom.

The preferred compounds of the invention are those in which $R_1$ and $R_2$ are both alkyl radicals. Amongst these compounds, those in which Y is in the 6-position and represents either a halogen atom or the methyl radical are particularly preferred. Finally, amongst the latter compounds, there may be mentioned those in which Z is a radical

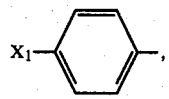

in which $X_1$ is a halogen atom or the radical $CH_3$.

According to a feature of the invention, the compounds of formula (I) can be prepared according to the following reaction scheme:

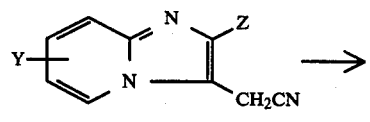
(II)

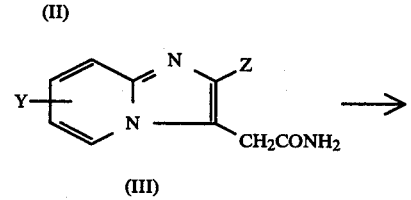
(III)

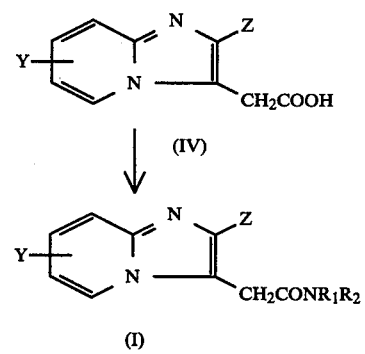
(IV)

(I)

The reaction for the conversion of the nitrile (II) to the primary amide is carried out in accordance with a conventional method, for example with the aid of an acid such as dry hydrogen chloride, in a solvent such as formic acid, at a temperature from 15° to 50° C.

The saponification of the primary amide (III) to the acid (IV) may be carried out in ethanolic potassium hydroxide at the reflux temperature.

The conversion of the acid (IV) to the amide compound of formula (I) is carried out in accordance with any suitable method, for example by reacting the acid (IV) with the amine $HNR_1R_2$, in the presence of carbonyldiimidazole, or by reacting the chloride of the acid (IV) with the amine $HNR_1R_2$.

The general method for the preparation of the starting nitriles (II) is described in the literature, in particular in British Pat. No. 1,076,089.

The following Examples illustrate the present invention. The analyses and the IR and NMR spectra confirm the structure of the compounds.

EXAMPLE 1

6-Chloro-2-(4-chlorophenyl)-imidazo[1,2-a]-pyridine-3-N, N-dimethylacetamide.

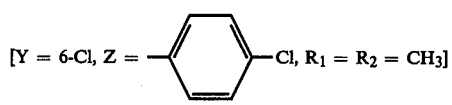

[Y = 6-Cl, Z = —⟨C_6H_4⟩—Cl, $R_1 = R_2 = CH_3$]

1. 22 g (0.0788 mol) of 6-chloro-2-(4-chlorophenyl)-imidazo[1,2-a]pyridine-3-acetonitrile are added to 85 ml of 99% formic acid and the solution is treated with a stream of dry hydrogen chloride for 3 to 4 hours. When all the nitrile has been converted, the solution is heated slightly to degas it, and the cooled solution is then poured into 1 liter of water; the mixture is stirred for 10 minutes and then rendered alkaline with 200 ml of concentrated ammonia solution. The solid is filtered off, washed copiously with water and dried under a water-pump vacuum. The 6-chloro-2-(4-chlorophenyl)-imidazo[1,2-a]pyridine-3-acetamide is recrystallised from ethanol. Melting point=285°-7° C.

2. 19.2 g of 6-chloro-2-(4-chlorophenyl)-imidazo[1,2-a]pyridine-3-acetamide and 19 g of KOH are added successively to 550 ml of 75% ethanol. The suspension is heated at the reflux temperature for 10-16 hours. When the reaction has ended, the solution is concentrated in vacuo and the residue is dissolved in ½ liter of water. The small amount of insoluble material is filtered off and the filtrate is treated with 50 ml of acetic acid. The expected acid precipitates and it is filtered of and roughly dried. The crude product is taken up in 500 ml of acetone and the 6-chloro-2-(4-chlorophenyl)-imidazo[1,2-a]pyridine-3-acetic acid is filtered off hot. Melting point=258°-260° C.

3. 4 g (12.45 millimols) of 6-chloro-2-(4-chlorophenyl)-imidazo[1,2-a]pyridine-3-acetic acid and 2.42 g (14.94 millimols) of carbonyldiimidazole are suspended in 60 ml of dry tetrahydrofuran. The reaction mixture is stirred at 20° C. until the evolution of carbon dioxide has ended, and is then heated gently at 40° C. for 15 minutes and cooled to 0° C. A solution of 14.94 millimols of dimethylamine in 5 ml of tetrahydrofuran is then added. The suspension is stirred for 15 minutes at 20° C. and then concentrated; the residue is treated with 300 ml of water and 50 ml of a saturated aqueous solution of NaHCO$_3$. The insoluble material is filtered off, washed with water and dried. The compound obtained is recrystallised from a solvent such as ethanol. Melting point=230° C.

EXAMPLE 2

4-Methyl-1-{[2-(4-chlorophenyl)-imidazo[1,2-a]pyridin-3-yl]methylcarbonyl}-piperazine.

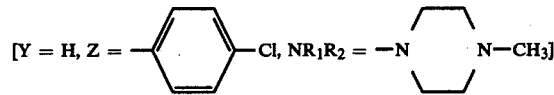

4.5 g (15.64 millimols) of 2-(4-chlorophenyl)-imidazo[1,2-a]pyridine-3-acetic acid are added to a suspension of N,N-dimethyl-chloro-methyleneiminium chloride prepared by adding 2.2 g (17.75 millimols) of oxalyl chloride to 30 ml of dimethylformamide (DMF) at −10° C. The suspension is stirred for 15 minutes at 0° C. and a solution of 5.4 g (54 millimols) of 4-methylpiperazine in 10 ml of dry DMF is then added gradually thereto at 0° C. The solution is stirred for 8 hours and then poured into 750 ml of water. The amide is extracted with CH$_2$Cl$_2$, the organic phase is dried over Na$_2$SO$_4$ and concentrated, the residue is passed through a silica column (eluant: CH$_2$Cl$_2$/CH$_3$OH 9/1) and the compound obtained is recrystallised from an isopropyl ether/acetonitrile mixture. Melting point=175° C.

The compounds listed in the following Table were similarly prepared.

TABLE

| Compound | Y | Z | NR$_1$R$_2$ | Melting point (°C.) |
|---|---|---|---|---|
| 1 | H | 4-Cl—C$_6$H$_4$ | —NHCH$_3$ | 234 |
| 2 | H | 4-Cl—C$_6$H$_4$ | —N(CH$_3$)$_2$ | 179 |
| 3 | H | 4-Cl—C$_6$H$_4$ | —N(pyrrolidine) | 187-8 |
| 4 | H | 4-Cl—C$_6$H$_4$ | —N(piperidine) | 190 |
| 5 | H | 4-Cl—C$_6$H$_4$ | —N(N-methylpiperazine) | 175 |
| 6 | H | 3-CF$_3$—C$_6$H$_4$ | —N(N-methylpiperazine) | 157.5-158 |

TABLE-continued

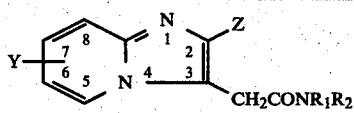

| Compound | Y | Z | NR₁R₂ | Melting point (°C.) |
|---|---|---|---|---|
| 7 | H | 4-Cl—C₆H₄ | —N(piperazinyl)-2-methoxyphenyl | 206-7 |
| 8 | H | 4-Cl—C₆H₄ | —N(morpholino) | 242 |
| 9 | 6-Cl | 4-Cl—C₆H₄ | —NHCH₃ | >290 |
| 10 | 6-Cl | 4-Cl—C₆H₄ | —NHC₂H₅ | 280-2 |
| 11 | 6-Cl | 4-Cl—C₆H₄ | —NH—n-C₃H₇ | 229-30 |
| 12 | 6-Cl | 4-Cl—C₆H₄ | —NH—i-C₃H₇ | 259 |
| 13 | 6-Cl | 4-Cl—C₆H₄ | —NH—n-C₄H₉ | 225 |
| 14 | 6-Cl | 4-Cl—C₆H₄ | —NH—t-C₄H₉ | 224 |
| 15 | 6-Cl | 4-Cl—C₆H₄ | —NH-cyclopentyl | 243-5 |
| 16 | 6-Cl | 4-Cl—C₆H₄ | —NHC₆H₅ | 265-7 |
| 17 | 6-Cl | 4-Cl—C₆H₄ | —NHCH₂C₆H₅ | 253-4 |
| 18 | 6-Cl | 4-Cl—C₆H₄ | —NHCH₂CH₂OH | 260-1 |
| 19 | 6-Cl | 4-Cl—C₆H₄ | —NHCH₂CH₂OCH₃ | 197 |
| 20 | 6-Cl | 4-Cl—C₆H₄ | —NHCH₂CH₂N(CH₃)₂ | 199-201 |
| 21 | 6-Cl | 4-Cl—C₆H₄ | —NHCH₂CH=CH₂ | 233 |
| 22 | 6-Cl | 4-Cl—C₆H₄ | —NHCH₂—C≡CH | 239 |
| 23 | 6-Cl | 4-CH₃—C₆H₄ | —NHC₂H₅ | 238 |
| 24 | 6-Cl | 4-Cl—C₆H₄ | —NHCH₂CF₃ | 258 |
| 25 | 6-Cl | 4-Cl—C₆H₄ | —NHCH₂CONH₂ | 256-7 |
| 26 | 6-Cl | 4-Cl—C₆H₄ | —N(CH₃)₂ | 230 |
| 27 | 6-Cl | 4-Cl—C₆H₄ | —N(C₂H₅)₂ | 149 |
| 28 | 6-Cl | 4-Cl—C₆H₄ | —N(n-C₃H₇)₂ | 140-1 |
| 29 | 6-Cl | 4-Cl—C₆H₄ | —N(CH₃)(n-C₃H₇) | 160 |
| 30 | 6-Cl | 4-Cl—C₆H₄ | —N(CH₃)(CH(CH₃)₂) | 185-6 |
| 31 | 6-Cl | 4-Cl—C₆H₄ | —N(n-C₄H₉)₂ | 149-150 |
| 32 | 6-Cl | 4-Cl—C₆H₄ | —N(azetidinyl) | 243-5 |
| 33 | 6-Cl | 4-Cl—C₆H₄ | —N(pyrrolidinyl) | 219-220 |
| 34 | 6-Cl | 4-Cl—C₆H₄ | —N(piperidinyl) | 208-9 |

TABLE-continued

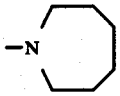

| Compound | Y | Z | NR₁R₂ | Melting point (°C.) |
|---|---|---|---|---|
| 35 | 6-Cl | 4-Cl—C₆H₄ | 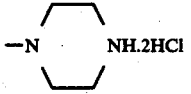 | 190–2 |
| 36 | 6-Cl | 4-Cl—C₆H₄ | 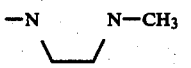 | >300 |
| 37 | 6-Cl | 4-Cl—C₆H₄ |  | 204–6 |
| 38 | 6-Cl | 4-Cl—C₆H₄ | 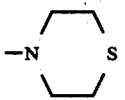 | 262 |
| 39 | 6-Cl | 4-Cl—C₆H₄ | 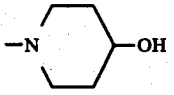 | 239–241 |
| 40 | 6-Cl | 4-Cl—C₆H₄ | 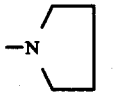 | 270 |
| 41 | 6-CH₃ | 4-Cl—C₆H₄ | —NHCH₃ | 261–2 |
| 42 | 6-CH₃ | 4-Cl—C₆H₄ | —NHC₂H₅ | 224–5 |
| 43 | 6-CH₃ | 4-Cl—C₆H₄ | —NH—CH₂CH₂OH | 246 |
| 44 | 6-CH₃ | 4-Cl—C₆H₄ | —N(CH₃)₂ | 215 |
| 45 | 6-CH₃ | 4-Cl—C₆H₄ | —NH—CH₂—CH₂—Cl | 202 |
| 46 | 6-CH₃ | 4-Cl—C₆H₄ | 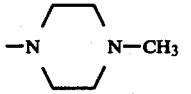 | 194 |
| 47 | 6-Cl | C₆H₅ | —NHCH₃ | 276–7 |
| 48 | 6-Cl | C₆H₅ | —N(CH₃)₂ | 192 |
| 49 | 6-Cl | 4-CH₃—C₆H₄ | —NHCH₃ | 277–8 |
| 50 | 6-Cl | 4-CH₃—C₆H₄ | —N(CH₃)₂ | 185–6 |
| 51 | 6-Cl | 4-CH₃O—C₆H₄ | —NHCH₃ | 273 |
| 52 | 6-Cl | 4-CH₃O—C₆H₄ | —N(CH₃)₂ | 166 |
| 53 | 6-Cl | 4-Br—C₆H₄ | —NHC₂H₅ | 287 |
| 54 | 6-Cl | 4-Br—C₆H₄ | —N(C₂H₅)₂ | 168 |
| 55 | 6-Cl | naphth-2-yl | 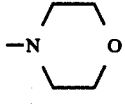 | 217–8 |
| 56 | 6-Cl | naphth-2-yl | 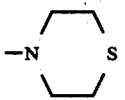 | 193–4 |
| 57 | 6-Cl | naphth-1-yl | —N(CH₃)₂ | 187–8 |
| 58 | 6-Cl | 2-CH₃—C₆H₄ | —NHCH₃ | 175–6 |
| 59 | 6-Cl | 2-CH₃—C₆H₄ | —NHC₂H₅ | 161–2 |
| 60 | 6-Cl | 2-CH₃O—C₆H₄ | —NHC₂H₅ | 172–3 |

TABLE-continued

| Compound | Y | Z | NR₁R₂ | Melting point (°C.) |
|---|---|---|---|---|
| 61 | 6-Cl | 3-Cl—C₆H₄ | —NHC₂H₅ | 215-6 |
| 62 | 6-Cl | 3-CH₃O—C₆H₄ | —N(C₂H₅)₂ | 98-9 |
| 63 | 6-Cl | 3-CH₃O—C₆H₄ | 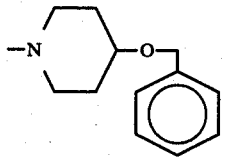 | 190 |
| 64 | 6-Cl | 3,4-Cl₂—C₆H₃ | —N(CH₃)₂ | 221-2 |
| 65 | 6-Cl | 3,4-(CH₃O)₂—C₆H₃ | —N(CH₃)₂ | 215 |
| 66 | 6-Cl | 3,4-(CH₃O)₂—C₆H₃ | —N(n-C₃H₇)₂ | 147 |
| 67 | 7-CH₃ | 4-Cl—C₆H₄ | —NHC₂H₅ | 228 |
| 68 | 7-CH₃ | 4-Cl—C₆H₄ | —N(CH₃)₂ | 206 |
| 69 | 8-CH₃ | 4-Cl—C₆H₄ | —NHCH₃ | 234 |
| 70 | 8-CH₃ | 4-Cl—C₆H₄ | —N(C₂H₅)₂ | 175,5 |
| 71 | 6-Cl | 4-F—C₆H₄ | —N(CH₃)₂ | 210 |
| 72 | 6-Cl | 4-F—C₆H₄ | —N(n-C₄H₉)₂ | 129 |
| 73 | 6-CH₃ | 4-F—C₆H₄ | —N(CH₃)₂ | 195 |
| 74 | 6-Cl | 4-Br—C₆H₄ | —N(CH₃)₂ | 228-9 |
| 75 | 6-CH₃ | 4-CH₃—C₆H₄ | —N(CH₃)₂ | 196 |
| 76 | 6-CH₃ | 4-Cl—C₆H₄ | —N(n-C₄H₉)₂ | 116 |
| 77 | 6-Cl | 4-Cl—C₆H₄ | 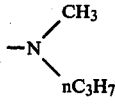 | 152 |
| 78 | H | 4-Cl—C₆H₄ | —N(n-C₃H₇)₂ | 136 |
| 79 | H | 4-Cl—C₆H₄ | —N(n-C₄H₉)₂ | 105 |
| 80 | 6-Cl | 4-Cl—C₆H₄ | —N(n-C₅H₁₁)₂ | 92-3 |
| 81 | 6-CH₃ | 4-CH₃—C₆H₄ | —NHCH₃ | 187 |
| 82 | 6-CH₃ | 4-CH₃—C₆H₄ | —NHC₂H₅ | 184 |
| 83 | 6-CH₃ | 4-CH₃C₆H₄ | —N(CH₃)(nC₃H₇) | 108 |
| 84 | 6-CH₃ | 4-CH₃C₆H₄ | —N(n-C₃H₇)₂ | 115 |
| 85 | 6-CH₃ | 4-CH₃—C₆H₄ |  | 168 |
| 86 | 6-CH₃ | 4-Cl—C₆H₄ | —NHCH₂CF₃ | 239 |
| 87 | 6-CH₃ | 4-Br—C₆H₄ | —NHC₂H₅ | 232-4 |
| 88 | 6-CH₃ | 4-Br—C₆H₄ | —N(CH₃)₂ | 203.5-205 |
| 89 | 6-CH₃ | 4-Br—C₆H₄ | —N(n-C₃H₇)₂ | 138-9 |
| 90 | 6-CH₃ | 4-Br—C₆H₄ |  | 195.5-197 |
| 91 | 6-CH₃ | 4-CH₃O—C₆H₄ | —N(CH₃)₂.CH₃SO₃H | 230-2 |
| 92 | 6-CH₃ | 4-CH₃S—C₆H₄ | —N(CH₃)₂.CH₃SO₃H | 209 |
| 93 | 6-CH₃ | 4-CH₃SO₂—C₆H₄ | —N(CH₃)₂ | 227-9 |
| 94 | 6-CH₃ | 4-NO₂—C₆H₄ | —NHC₂H₅ | 268-270 |
| 95 | 6-CH₃ | 4-NO₂—C₆H₄ | —N(CH₃)₂ | 262-3 |
| 96 | 6-CH₃ | 4-t-C₄H₉—C₆H₄ | —N(CH₃)₂ | 199-200 |

TABLE-continued

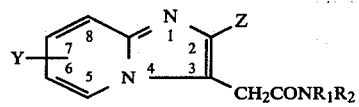

| Compound | Y | Z | NR₁R₂ | Melting point (°C.) |
|---|---|---|---|---|
| 97 | 6-Cl | 4-Cl—C₆H₄ | —N(CH₃)(C₂H₅) | 173 |

The compounds of the invention were subjected to pharmacological experiments which showed their valuable pharmacological properties in various areas.

The toxicity of the compounds was determined on mice by intraperitoneal administration. The LD 50 ranges from 500 to 1,000 mg/kg.

The anxiolytic activity was determined according to the eating test (R. J. Stephens, (1973), Brit. J. Pharmac., 49, 146 P). In this test, the doses which increases the food consumption of the mice vary from 0.1 to 10 mg/kg, administered intraperitoneally.

The activity of the compounds in the area of cerebral circulation was determined in the test for the hypoxia caused by pressure reduction. Mice of the CD1 strain are kept in an oxygen-depleted atmosphere produced by creating a partial vacuum (190 mm of mercury, corresponding to 5.25% of oxygen). The survival time of the animals is noted. This time is increased by agents which are capable of assisting the oxygenation of tissues and in particular of the brain. The compounds studied are administered intraperitoneally in several doses, 10 minutes before the experiment. The percentage increases in the survival time, relative to the values obtained for control animals, are calculated. The mean active dose (MAD), that is to say the dose which increases the survival time by 100%, is determined graphically. The MAD ranges from 0.3 to 32 mg/kg, administered intraperitoneally.

The anticonvulsant activity was determined in accordance with the test for the antagonism towards the mortality induced by bicuculline in mice (P. Worms, H. Depoortere and K. G. Lloyd, (1979) Life Sci., 25, 607–614). The products to be studied are injected intraperitoneally, 30 minutes before the bicuculline (0.9 mg/kg, administered intravenously). With death being the criterion selected for this test, the percentage mortalities are noted for each batch, 2 hours after administration of the bicuculline (control batch: 100% mortality). For each product, the 50% active dose (AD 50 or the dose which protects 50% of the animals from the lethal effects of the bicuculline) is determined graphically. The AD 50 of the compounds of the invention vary between 0.3 and 30 mg/kg, administered intraperitoneally.

The sedative or hypnotic activity was determined by observing the action of the compounds on the EEG of curarised rats and also on the wake-sleep states in freely moving, implanted rats and cats (H. Depoortere, Rev. E.E.G. Neurophysiol., (1980) 10, 3, 207–214; L. M. Da Costa, H. Depoortere and R. Naquet, Rev. E.E.G. Neurophysiol., (1977), 7, 2, 158–164). In curarised rats, the products to be studied were injected intraperitoneally or orally at doses increasing from 0.1 to 30 mg/kg. They induce sleep traces starting from doses ranging from 0.1 to 10 mg/kg, administered intraperitoneally or orally. In freely moving, implanted rats, the products to be studied were injected intraperitoneally or orally at a single dose ranging from 1 to 10 mg/kg. At these doses, they reduce the total wake time by 13 to 44%, without significantly changing the total paradoxical sleep time, certain products even increasing the total duration of this phase of sleep. In freely moving, implanted cats, the products to be studied were injected intraperitoneally or orally at a single dose of 10 mg/kg. They transitorily increase the wake time after injection, this being accompanied by benzodiazepine-type jactation, and reduce the total paradoxical sleep time by 40 to 100%. However, certain products increase the total duration of the SWSP (slow-wave sleep with phase phenomena: P.G.O. points) by about 50%.

The results of these various tests show that the compounds of the invention possess anxiolytic, anti-anoxic, sleep-inducing, hypnotic and anticonvulsant propertis; the compounds of the invention are useful for the treatment o anxiety states, sleep disorders and other neurological and psychiatric complaints, for the treatment of vigilance disorders, in particular for combating behavioural disorders which can be attributed to cerebral vascular damage and to the cerebral sclerosis encountered in geriatrics, and also for the treatment of epileptic vertigo due to cranial traumatisms and for the treatment of metabolic encephalopathies.

The compounds of the invention can be presented in any form which is suitable for oral or parenteral administration, for example in the form of tablets, coated tablets, capsules, solutions to be taken orally or injected, and the like, with any suitable excipient. The daily posology can range from 0.5 to 2,000 mg.

What is claimed is:

1. A compound of the formula

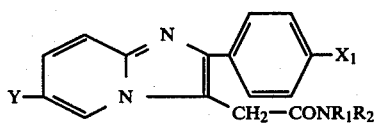

wherein
$X_1$ is halogen or methyl;
Y is hydrogen, halogen or methyl;
$R_1$ is hydrogen, $C_{1-5}$ alkyl or hydroxy ($C_{1-5}$ alkyl); and
$R_2$ is $C_{1-5}$ alkyl or hydroxy ($C_{1-5}$ alkyl)
or a pharmaceutically acceptable salt thereof.

2. An imidazo[1,2-a]pyridine according to claim 1, in which $R_1$ and $R_2$ are both alkyl radicals.

3. An imidazo[1,2-a]pyridine according to claim 2, in which Y is chlorine or methyl.

4. A method of providing a patient with a hypnotic effect which comprises administerinng to said patient a hypnotically-effective amount of a compound of the formula:

wherein
- $X_1$ is halogen or methyl;
- Y is hydrogen, halogen or methyl;
- $R_1$ is hydrogen, $C_{1-5}$ alkyl or hydroxy ($C_{1-5}$ alkyl); and
- $R_2$ is $C_{1-5}$ alkyl or hydroxy ($C_{1-5}$ alkyl)

or a pharmaceutically acceptable salt thereof.

5. A method of claim 4 wherein $R_1$ and $R_2$ are alkyl.

6. A method of claim 5 wherein Y is chlorine or methyl.

7. A method of providing a patient with an anxiolytic effect which comprises administering to said patient an anxioloytically-effective amount of a compound of the formula:

wherein
- $X_1$ is halogen or methyl;
- Y is hydrogen, halogen or methyl;
- $R_1$ is hydrogen, $C_{1-5}$ alkyl or hydroxy ($C_{1-5}$ alkyl); and
- $R_2$ is $C_{1-5}$ alkyl or hydroxy ($C_{1-5}$ alkyl) or a pharmaceutically acceptable salt thereof.

8. A method of claim 7 wherein $R_1$ and $R_2$ are alkyl.

9. A method of claim 8 wherein Y is chlorine or methyl.

10. A method of providing a patient with an anticonvulsive effect which comprises administering to said patient an anticonvulsive dosage of a compound of the formula:

wherein
- $X_1$ is halogen or methyl;
- Y is hydrogen, halogen or methyl;
- $R_1$ is hydrogen, $C_{1-5}$ alkyl or hydroxy ($C_{1-5}$ alkyl); and
- $R_2$ is $C_{1-5}$ alkyl or hydroxy ($C_{1-5}$ alkyl) or a pharmaceutically acceptable salt thereof.

11. A method of claim 10 wherein $R_1$ and $R_2$ are alkyl.

12. A method of claim 11 wherein Y is chlorine or methyl.

* * * * *

UNITED STATES PATENT AND TRADEMARK OFFICE

CERTIFICATE EXTENDING PATENT TERM
UNDER 35 U.S.C. § 156

PATENT NO.: 4,382,938

DATED: May 10, 1983

INVENTORS: Jean-Pierre Kaplan et al.

PATENT OWNER: Synthelabo

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

5 YEARS with all rights pertaining thereto as provided by 35 U.S.C. § 156(b).

I have caused the seal of the Patent and Trademark Office to be affixed this 20th day of September 1994.

Bruce A. Lehman
Assistant Secretary of Commerce and
    Commissioner of Patents and Trademarks